United States Patent
Kim-Berman

(10) Patent No.: US 9,216,103 B2
(45) Date of Patent: Dec. 22, 2015

(54) EXTRAORAL NASAL MOLDING HEADGEAR DEVICE FOR THE TREATMENT OF CLEFT LIP AND PALATE

(71) Applicant: Hera Kim-Berman, Roslyn Heights, NY (US)

(72) Inventor: Hera Kim-Berman, Roslyn Heights, NY (US)

( * ) Notice: Subject to any disclaimer, the term of this patent is extended or adjusted under 35 U.S.C. 154(b) by 66 days.

(21) Appl. No.: 14/154,847

(22) Filed: Jan. 14, 2014

(65) Prior Publication Data

US 2015/0164676 A1 Jun. 18, 2015

Related U.S. Application Data

(60) Provisional application No. 61/916,624, filed on Dec. 16, 2013.

(51) Int. Cl.
| | | |
|---|---|---|
| *A61F 5/08* | (2006.01) | |
| *A61B 17/24* | (2006.01) | |
| *A61F 5/058* | (2006.01) | |

(52) U.S. Cl.
CPC . *A61F 5/08* (2013.01); *A61B 17/24* (2013.01); *A61F 5/05891* (2013.01)

(58) Field of Classification Search
CPC ........ A61F 5/08; A61F 5/05891; A61B 17/24
USPC ............... 606/191, 196, 199, 204.15, 204.45; 600/237; 602/17, 32, 34, 35, 36; 433/5
See application file for complete search history.

(56) References Cited

U.S. PATENT DOCUMENTS

| | | | | |
|---|---|---|---|---|
| 1,100,991 | A | * 6/1914 | Rostow | 606/204.45 |
| 1,372,089 | A | * 3/1921 | Rostow | 606/204.45 |
| 2,151,458 | A | * 3/1939 | Allen | 602/17 |
| 2,681,058 | A | * 6/1954 | Mathues | 602/17 |
| 3,895,624 | A | 7/1975 | Georgiade | |
| 3,927,664 | A | * 12/1975 | Georgiade et al. | 606/54 |
| 4,157,085 | A | 6/1979 | Austad | |
| 4,195,046 | A | 3/1980 | Kesling | |
| 4,842,515 | A | 6/1989 | Zeiser | |

(Continued)

FOREIGN PATENT DOCUMENTS

EP 1 322 243 B1 10/2005

OTHER PUBLICATIONS

Ortho Technology, Inc., Multi-Adjustable Facemask®, http://www.orthotechnology.com/new_products/facemask.cfm, printed Aug. 26, 2013, 3 pages.

(Continued)

*Primary Examiner* — Jing Ou
(74) *Attorney, Agent, or Firm* — Brad M. Beehar & Associates, PLLC

(57) ABSTRACT

The present invention is a device for pre-surgical treatment of cleft lip and cleft palate. The device is extraoral thus reducing the risk associated with existing devices and technologies that are intraoral, such as, for example utilizing a Nasoalveolar Molding (NAM) appliance. The adjustable extraoral nasal molding appliance of the present invention consists of an adjustable and securable head fastener, a front connector with a forehead rest pad, a rod support having an aperture through which a rod is slidably connected, a fastener for locking a rod in a set position, the rod, a spring and at least one nasal bulb. Different shaped springs can be attached for treating unilateral as well as bilateral cleft lip and palate patients. Different nasal bulbs can be attached for treating unilateral as well as bilateral cleft lip and palate patients.

15 Claims, 4 Drawing Sheets

(56) References Cited

U.S. PATENT DOCUMENTS

| | | |
|---|---|---|
| 4,856,663 A | 8/1989 | Epp |
| D308,096 S | 5/1990 | Collins, Jr. |
| 5,466,152 A | 11/1995 | Walter |
| 5,810,583 A * | 9/1998 | Doyle .................. 433/5 |
| 5,890,891 A * | 4/1999 | Doyle .................. 433/5 |
| 5,922,006 A * | 7/1999 | Sugerman .......... 606/204.45 |
| 6,773,451 B1 | 8/2004 | Dussere |
| 7,328,077 B2 | 2/2008 | Durbin et al. |
| 7,909,606 B2 | 3/2011 | Marcello |
| 2004/0199094 A1 * | 10/2004 | Greene et al. ............ 602/17 |
| 2008/0305453 A1 | 12/2008 | Kitching et al. |
| 2009/0062706 A1 * | 3/2009 | Phillips ................. 602/19 |
| 2009/0099657 A1 * | 4/2009 | Hopper .................. 623/10 |
| 2011/0060438 A1 | 3/2011 | Stoddard et al. |
| 2012/0028204 A1 | 2/2012 | Lazarou |
| 2012/0148970 A1 | 6/2012 | Kassap |
| 2012/0221044 A1 | 8/2012 | Archibald et al. |
| 2014/0121696 A1 * | 5/2014 | Kaczperski et al. ..... 606/204.45 |

OTHER PUBLICATIONS

Nasal Alveolar Molding (NAM)—Children's Healthcare of Atlanta, http://www.choa.org/childrens-hospital-services/pediatric-craniofacial . . . , printed Aug. 23, 2013, p. 1 of 2.

ODP, Inc.—Multi-Adjustable Facemask, http://www.odpinc.com/page.php?s=products&c=extraoral&p=facemask, printed Aug. 26, 2013, 3 pages.

Headgear and Supplies, www.orthospecialties.com, date printed unknown, source unknown, 5 pages.

\* cited by examiner

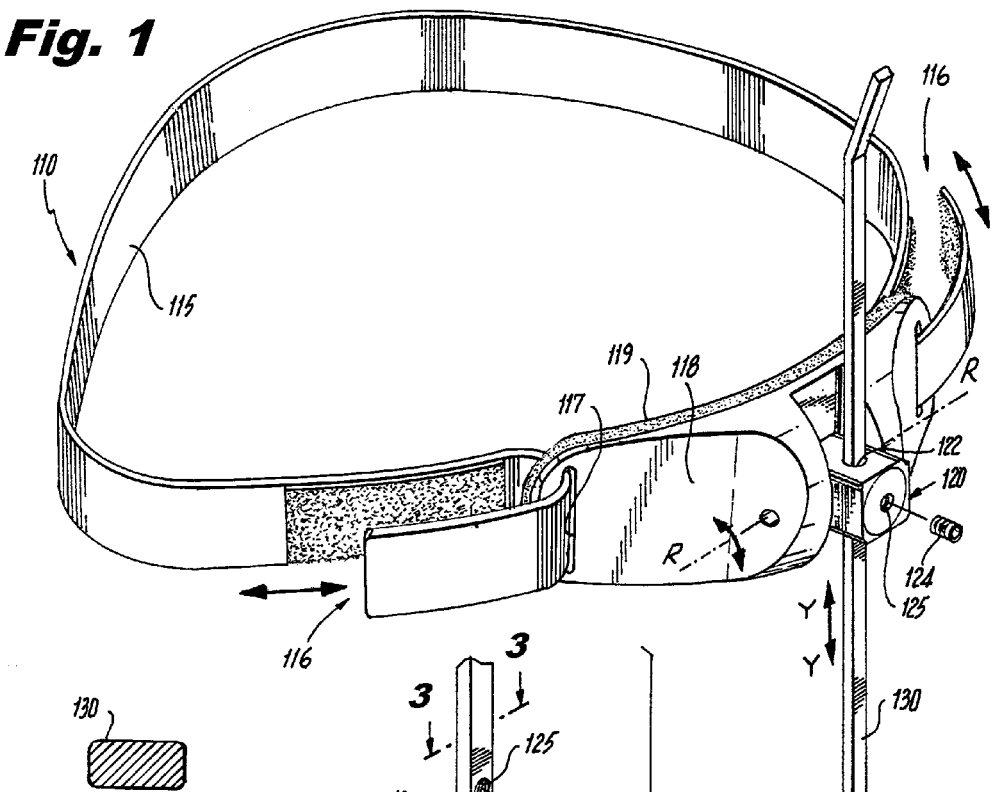
Fig. 1
Fig. 3
Fig. 4
Fig. 5
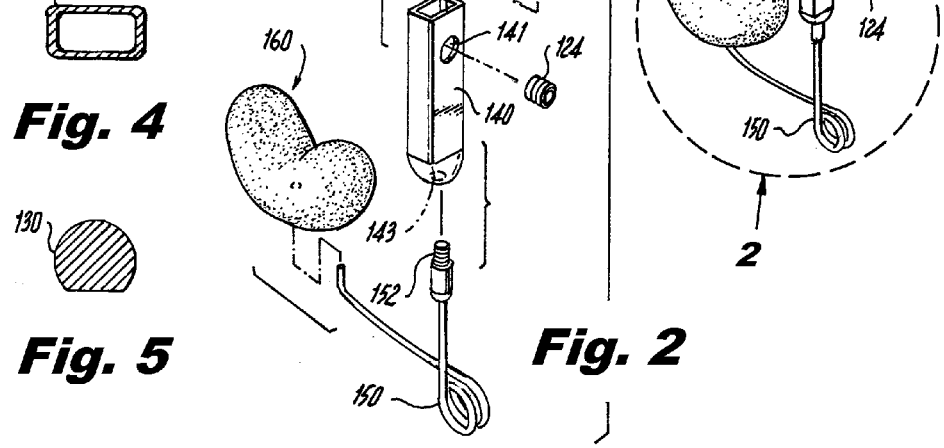
Fig. 2

EXTRAORAL NASAL MOLDING HEADGEAR DEVICE FOR THE TREATMENT OF CLEFT LIP AND PALATE

CROSS-REFERENCE TO RELATED APPLICATION

This non-provisional patent application claims the benefit of U.S. Provisional Patent Application Ser. No. 61/916,624 filed on Dec. 16, 2013 which is expressly incorporated herein in its entirety by reference thereto.

FIELD OF THE INVENTION

The present invention relates generally to devices and appliances used to treat cleft lip and palate prior to corrective surgery. The present invention relates to orthodontics and orthopedics for lip and palate closure. The present invention relates further to head fastening devices. The present invention also relates to appliances and equipment that are supported from head straps and hats.

BACKGROUND OF THE INVENTION

Orofacial clefts are among the most common congenital anomalies with prevalence of about one out of every seven hundred births in the United States. Throughout their lives, children who have an orofacial cleft need several surgical procedures and complex medical treatments requiring various medical and dental specialists.

Studies support the use of pre-surgical infant orthopedic treatment, such as a Nasoalveolar Molding (NAM) appliance, to create a more aesthetic result after primary lip closure in patients with cleft lip and palate deformities. Studies have also shown improved nasal symmetry with the use of a nasal molding appliance following primary closure of the lip. In the neonate, temporary plasticity of the alar cartilages exists due to higher levels of hyaluronic acid circulating in the infant which allows for orthopedic changes. NAM appliance works to stretch and contour the alar tissue and the columella while bringing the palatal shelves into closer approximation.

The modern school of pre-surgical orthopedic treatment of the cleft lip and palate patient started in the 1950's where series of intraoral plates were used to mold the alveolar segments together. In 1993, nasal bulb attachments were utilized in conjunction with the plate to mold the lip, nose and the alveolus in neonates prior to lip repair.

The method of fabrication of the NAM appliance starts with an initial impression of the infant's palate. The materials commonly used for the impression of the palate are: alginate, polyvinyl siloxane, aluwax, and compound materials. Patients are evaluated for potential airway complications. Stock or customized trays are used to load the impression material. The infant is positioned upright and the tray/impression material is placed in the infant's mouth until the material is set. The tray is removed and the patient's mouth is suctioned and inspected to make sure no material remains in the oral or nasal cavity. The impression is poured up with stone and the plate is fabricated using an acrylic material. The tray is then tried in the patient and lined using a softer denture reline material for better comfort and fit. The nasal stent is fabricated chairside using stainless steel orthodontic wire with a helical design. An acrylic nasal bulb in the shape of a ball is fashioned and the stent is imbedded using acrylic to the fabricated plate. The plate with the nasal stent is inserted and the upper lip is taped using tape to act as a prolabial band. The bulb is positioned inside the nasal passage such that pressure is applied against the alar tissue and the columella causing growth and reducing the cleft. Due to the position of the spring and it being supported from the NAM appliance in the infant's mouth the resulting force applied is primarily medial (toward the centerline of the face) superior (upward) and anterior (away from the face).

The patient is seen in the office or hospital setting on two separate visits for the fabrication of the appliance and the appliance is adjusted every 1-2 weeks until the patient is determined to be ready for primary lip closure surgery. The average time of lip closure in infants can range from 4-6 months.

The custom fabrication of the NAM appliance, doctor time, and weekly appointments for NAM adjustments, make the procedure time consuming, technique sensitive, and expensive. Trained clinicians are also difficult to find. The primary professionals, typically pediatric dentists or orthodontists, who perform pre-surgical infant orthopedics on neonates with cleft lip and palate are usually associated with large hospitals or dental schools and universities. Due to the very time consuming nature of the current NAM fabrication process, potential airway complications, and numerous appointments, there is a need for a more universal appliance that can be adjustable and can be utilized in any medical provider's office or setting with minimal training.

Therefore, it is an object of the present invention to provide an improvement over existing intraoral nasal molding devices/appliances. It is the object of the invention to provide an extraoral device/appliance that can be more easily fitted and adjusted, is more convenient and comfortable, and provides safer and better treatment. It is an object of the present invention to provide an adjustable extraoral appliance that can be fitted to the infant and adjusted without the need for an impression of the maxilla resulting in less risk than NAM devices. There is a need for a device that can be provided to parents with less consumption of doctor time than existing technologies (less office visits)—an easier to size/fit device. There is a need for a less costly and resource consuming device. There is a need for a universal, adjustable, extraoral nasal molding appliance that can be utilized in many rural areas and underserved countries where access to healthcare, and qualified medical and dental professionals are limited. There is also a need for a better performing appliance capable of applying greater forces in the desired directions/vectors.

SUMMARY OF THE INVENTION

The adjustable extraoral nasal molding appliance of the present invention consists of an adjustable and securable head fastener, a front connector with a forehead rest pad, a rod support having an aperture through which a rod is slidably connected, a fastener for locking the slidable rod in a set position, a rod, a spring and a nasal bulb. Different shaped and sized springs can be attached. Different shaped and sized nasal bulbs can be attached for molding of unilateral as well as bilateral cleft lip and palate. The device is safer than NAM devices for pre-surgical treatment and closure of cleft lip and palate because it is completely extraoral.

While the invention will be described in connection with certain embodiments, it will be understood that the invention is not limited to those embodiments. To the contrary, the invention includes all alternatives, modifications and equivalents as may be included within the spirit and scope of the present invention.

The head fastener includes an easy to secure head band adjustable in size preferably using hook and loop material. Alternatively, buttons or other fastening devices can be used to adjust the size of the band. The head fastener includes a front connector that gets positioned near the middle of the infant's forehead when the head fastener is secured on the head. The inside of the head fastener preferably includes a pad or other component, such as, for example, gel strips, to reduce discomfort during use.

In the preferred embodiment, a rod support is fixedly attached to the outside of the front support. The rod support includes an aperture through its length such that a rod can slide up and down with respect to the fastener, rod support, and/or the front support. This slidability allows for the placement and adjustment of the bulb in the nasal passage and the forces exerted on the infant using the device. Alternatively, the rod support may be removably attached to the front support with a screw or other removable fastening structure. In such an embodiment, the rod may be fixedly attached to the rod support. Alternatively, the position of rod support may be adjustable on the front support.

In the preferred embodiment the rod support does not allow the rod to rotate with respect to the rod support although such an embodiment with the ability to rotate and lock in a desired rotational position is included within the scope of the invention.

With the rod attached to the rod support, the front support and rod is positioned in the middle of the infant's face with the rod between the eyes for the least obstruction of the infant's vision. The first end of the rod is inserted into the aperture in the rod support and locked into position at the desired height using a fastener such as a set screw or the like.

The second end of the rod includes a spring and a bulb. The first end of the spring may be fixedly attached or removably attached to the second end of the rod. The connection between the second end of the rod and the first end of the spring may provide for height adjustment of the bulb. In one embodiment of the invention, a connector may be provided between the second end of the rod and the first end of the spring. The connector can be configured for a single spring and bulb or for two springs and bulbs for bilateral cleft lip and palate treatment.

The spring when strained, provides a resistive force needed for pressure (force) on the alar tissue and columella in the desired direction(s) to help reshape nasal tissues and the lip which in turn will reshape the maxilla through growth. The spring is preferably a two or three coil steel wire that can be stretched, bent and/or reshaped to provide a variable distance for activation of the bulb(s) on the infant initially and during the course of the treatment period. In one embodiment, alternatively, during treatment, the spring can be removed and replaced with a different spring. The second end of the spring is attached to the bulb, preferably near the bottom/underside of the bulb (eg. middle of convex side of a kidney shaped bulb) to try to prevent the metal spring from directly contacting the facial tissue/skin.

The bulb(s) may be configured in a variety of shapes and sizes and can be constructed from a variety of materials. Preferably the bulb is kidney shaped to help prevent direct contact of the spring with the facial tissue/skin and for application of forces at the preferred locations.

BRIEF DESCRIPTION OF THE DRAWINGS

The accompanying drawings, which are incorporated in and constitute a part of this specification, illustrate embodiments of the invention and, together with the general description of the invention given above and the detailed description of an embodiment given below, serve to explain the principles of the present invention. Similar components of the devices are similarly numbered for simplicity.

FIG. 1 is a perspective view of one embodiment of the device according to the present invention with an adjustable and securable head fastener, a front connector with a forehead rest pad, a hinged rod support having an aperture through which a rod is slidably connected, a fastener for locking a slidable rod in a set position, a rod, a rod connector, a double helical spring and a nasal bulb.

FIG. 2 is an enlarged and exploded perspective view taken at arrow 2 in FIG. 1 showing part of the rod, a removable lockable rod connector, a removable double helical spring and a removable nasal bulb.

FIG. 3 is a sectional view of the rod shown in FIGS. 1 and 2 taken as section line 3-3 in FIG. 2.

FIG. 4 is a sectional view of an alternative rod configuration.

FIG. 5 is a sectional view of an alternative rod configuration with a flat side.

DETAILED DESCRIPTION OF THE INVENTION

Referring to the Figures, the invention consists of a fastener 110 for securing the appliance/device to the head 111 of an infant, preferably around the circumference of the head 111. The fastener 110 is adjustable in size and it is also removable.

Figure 6:
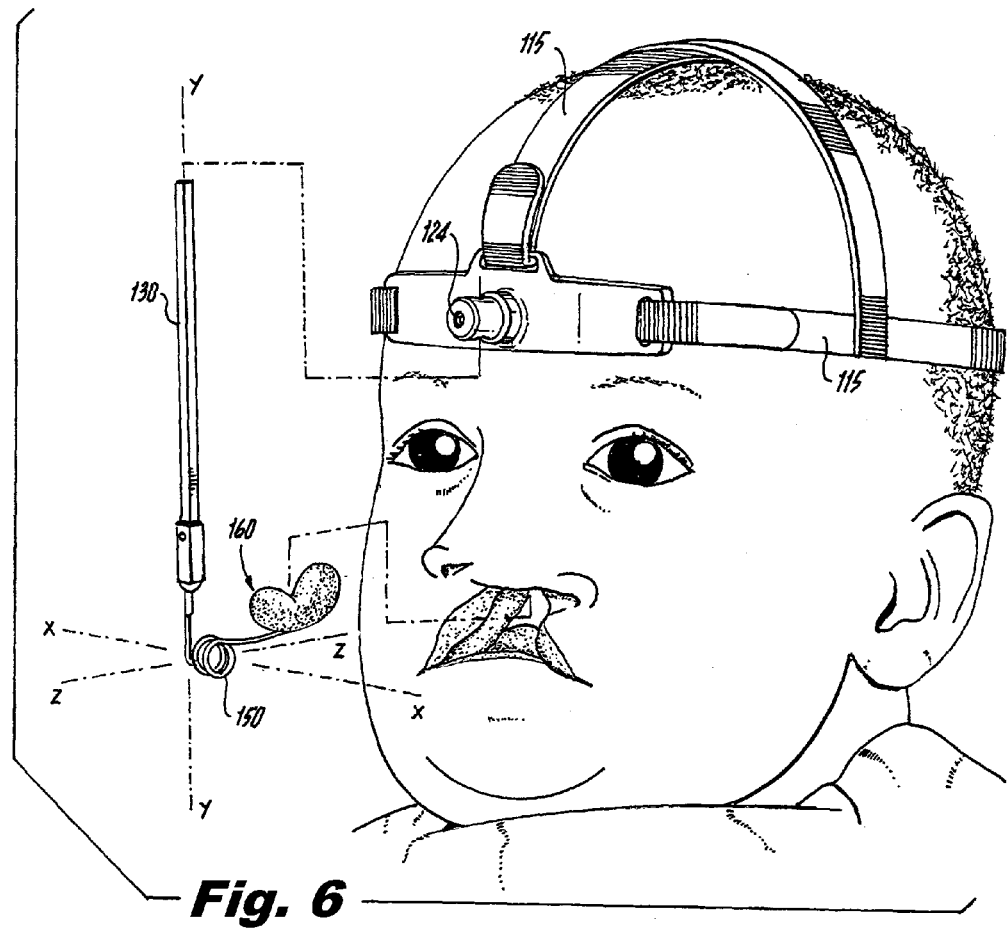
FIG. 6 is a perspective view of an alternative embodiment of the invention shown worn on the head of an infant. The head fastener includes an addition strap over the top of the head from the front to the back of the head strap. The rod support is not hinged in this embodiment. Axes X-X, Y-Y, and Z-Z are shown originating at the spring.
Figure 8:
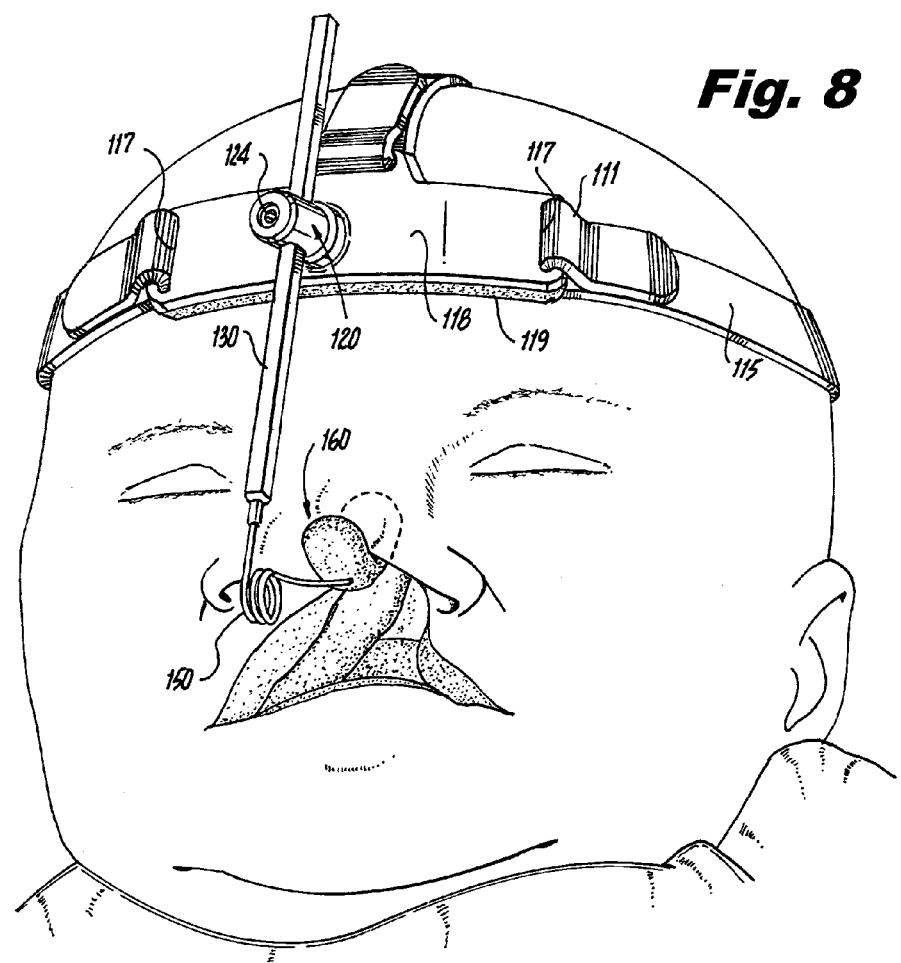
FIG. 8 is a front perspective view of another embodiment of the device according to the present invention shown on the head of an infant with the bulb in position in the nasal passage. The device shown includes an adjustable and securable head fastener, a front connector with a forehead rest pad, a rod support having an aperture through which a rod is slidably connected, a fastener for locking a slidable rod in a set position, a rod, a triple helical spring and a nasal bulb.
Figure 10:
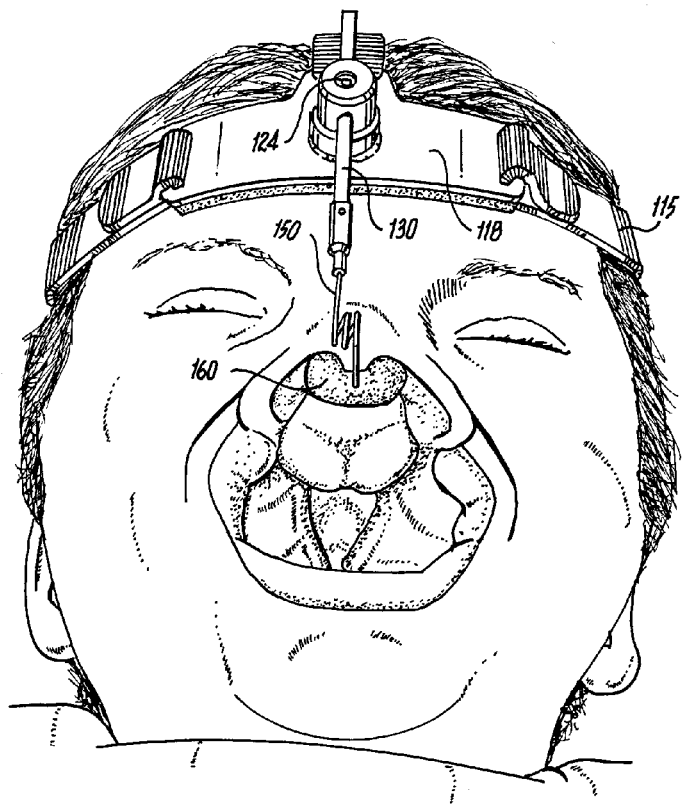
FIG. 10 is a front perspective view of another embodiment of the device according to the present invention shown on the head of an infant with bilateral cleft lip and palate with a U-shaped bulb in position within both nasal passages. The device shown includes an adjustable and securable head fastener, a front connector with a forehead rest pad, a rod support having an aperture through which a rod is slidably connected, a fastener for locking a slidable rod in a set position, a rod, a rod connector, a double helical spring and a bilateral nasal bulb.

For example, an elastic head band can be used as a fastener. More preferably, the fastener 110 comprises a non-elastic, adjustable band 115 that more securely attaches to the head 111 of the infant. A non-elastic fabric band 115 with a fastening means, e.g., buttons, hook and loop material (Velcro) 116, etc., can be used. As shown in the Figures, the band 115 may loop through a slot 117 in a front connector 118 which includes a pad 119. Other fasteners can include hats that cover the head of the infant, a fabric band that circumscribes the head of the infant with one or more straps connecting portions of the band on opposite sides of the head and transversing over the top of the head as shown in FIGS. 6, 8, and 10, as well as other fastening devices that may attach to the forehead of the infant without any structure around the entire head, such as, for example, a fastener 110 with adhesive or a pad that fastens to the forehead of the infant using adhesive or using tape.

Preferably, the fastener 110 comprises a comfort pad (forehead/glabella rest) 119 where the front of the fastener contacts the forehead of the infant. Preferably, pad 119 is positioned on the inside portion of a front connector 118 such that when the device is worn, the front connector 118 is located near the middle of the forehead of the infant. It is understood that additional pads 119 can be included on the fastener 110 or front connector 118 and/or additional connectors 118 may be positioned at other parts of the device, such as, for example, at the sides and/or the back of the head of the infant. In the preferred embodiment, the fastener 110 includes a front connector 118.

According to one embodiment of the invention, the fastener 110 includes a rod support 120 fixedly attached to the front connector 118. Most preferably, the rod support 120, is fixedly attached to the outside portion of the front connector 118 as viewed when the device is worn as shown in the figures, although the rod support 120 could be located on the inside of the rod support 118.

In the embodiment shown in FIGS. 1-3, the rod support 120 is attached to the front connector 118 in a hinged manner such that the rod support 120 can rotate about axis R-R. In such an embodiment it is desirable to be able to lock the hinge in a certain position, such as, for example, a stop mechanism or pin, or gear, etc. Most preferably, the rod support 120 does not rotate with respect to the front connector 118 and is fixedly attached without any hinge mechanism such as shown in FIGS. 6-12.

As shown in FIG. 1, rod support 120 comprises an aperture 122 though its length. The aperture 122 allows for a slidable connection with a rod 130 which can be secured at a desired height using a locking device, such as, for example, as shown in FIGS. 1-2, the set screw 124 with a threaded hole 125 in the rod support 120. With rod 130 placed in the aperture 122, the rod 130 can slide up and down with respect to the rod support 120 along the length of the rod in the Y-Y axis. Other locking devices for the rod 130 are included in the scope of the invention including pins, clamps and the like. Where the locking device is a set screw 124, the rod 130 preferably comprises at least one flat surface for connection to the end of the set screw 124. Rod 130 may also include indentations (not shown) along its length where the end of the set screw 124 can connect. As shown in FIGS. 3, 4, and 5, the rod 130 can be a variety of cross sectional shapes including rectangular, mostly circular, as well as triangular, pentagonal and other geometric shapes. Rod 130 can be a solid rod or more preferably to help reduce the weight of the device, rod 130 can be hollow. Rod 130 can be made of metal or other materials, e.g., plastic, with rigidity and strength. Rod 130 is preferably linear/straight along its length but can also be non-linear for improved ergonomics, comfort and/or infant visibility.

The slidability of the rod 130 in the Y-Y axis allows for ease of installation of the device on the infant. It is understood, however, that rod 130 need not be slidably attached to the rod support 120. Alternatively, the device can include a plurality of rods of various lengths and the rod 130 of desired length for a particular infant can be selected through trial and error and fastened to the rod support 120 using, for example, a screw, pin or other fastener.

In yet a further embodiment, the rod 130 may be fixedly attached to the rod support 120 which is removably attachable to the front connector 118. In such an embodiment, the desired length for the rod support 120 and the rod 130 can be selected from a plurality of different lengths that are prefabricated.

Figure 7:
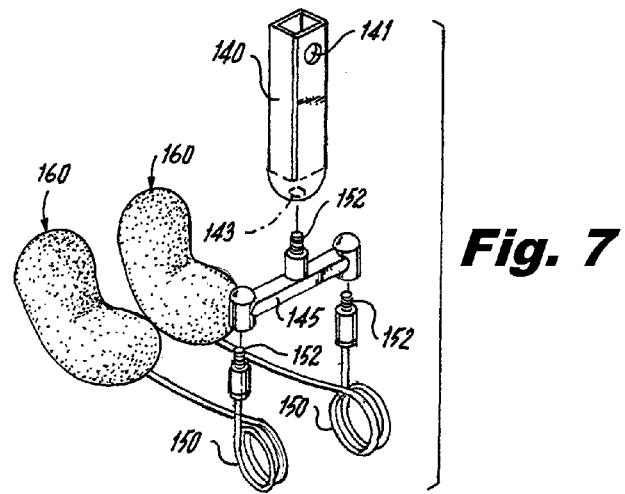
FIG. 7 is a partial perspective view of a partial view of an alternative embodiment of the invention for a bilateral cleft lip and palate showing a bilateral adaptor for connection to two springs and bulbs.

At the lower end of rod 130 is at least one spring 150 and at least one bulb 160 attached to the at least one spring 150. The spring 150 can be fixedly attached to the rod 130 or removably attached to the rod 130. For example, the end of spring 150 may insert into a hole (not shown) in the end of rod 130. Alternatively, the end of spring 150 comprises a screw 152 (such as for example as shown in FIG. 2) that threads into a receiving threaded hole (not shown in figures) in the end of rod 130. In the embodiments shown in FIGS. 1, 2, 6, 7, and 10-12, a connector 140 enables easier removal of the spring 150 and bulb 160 from rod 130, although the inclusion of the connector 140 is not necessary as shown in the embodiment in FIGS. 8 and 9. The connector 140 shown in the figures, with a bilateral adapter 145 as shown in FIG. 7, provides for easy modification of the device for a bilateral treatment with two springs 150 and two bulbs 160. In an embodiment comprising a threaded opening in the bottom of rod 130, the bilateral adapter 145 can thread directly into the bottom of the rod 130 without use of a connector 140. Connector 140 can be configured in a sleeve type configuration to slide over the exterior of the second end of rod 130 as shown in FIG. 2. In such a configuration, the connector 140 can be attached to the rod using a set screw 124 with or without a corresponding hole 125 and/or holes/indentations 125 in rod 130. The bottom of connector 140 includes a receiving threaded hole 143 for attachment to the spring 150. Connector 140 provides another way to adjust the height of the device and the bulb(s) 160 with respect to the infant when the device is worn.

Figure 9:
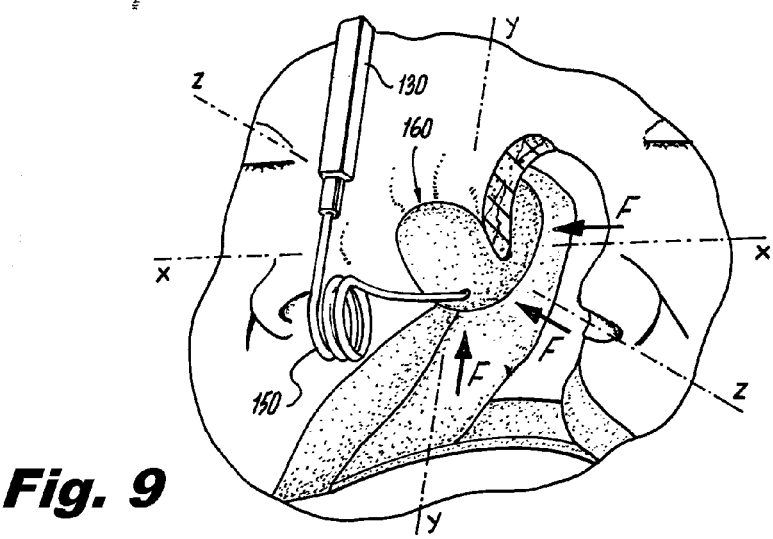
FIG. 9 is an enlarged, partial and cut perspective view of the bottom of the rod, the spring, the bulb and face of the infant shown in FIG. 8. The bulb is shown in a desired location inside and outside the nasal passage. The desired component forces (F) on the nasal tissue and lip are shown on the X, Y, and Z axes.

The spring 150 at the end of the rod 130, when strained, provides a resistive force needed to help apply pressure on the alar tissue and columella in the desired direction(s) and thus help reshape the tissue and lip which in turn will reshape the maxilla through growth. The use of a spring 150 and the ability to reshape the spring 150 and/or easily modify its configuration provides flexibility in all three axes X, Y, and Z (in all directions). A triple helical coil spring 150, as shown in FIGS. 8 and 9, is most preferred to provide the desired spring force and for ease with modification of the spring 150 configuration. The three coil spring 150 provides a high degree of flexibility for modification of the location of the bulb. The spring 150 coils can be stretched/modified to provide a great distance for activation of the bulb(s) on the infant initially and during the course of the treatment period. Other spring configurations, including double helical coils (also shown in the figures), single helical coils, zig-zag configurations, and other geometries are also possible and included in the scope of the invention. Use of two springs 150 is also possible for a bilateral case.

Bulb(s) 160 may be configured in a variety of shapes and sizes and can be constructed from a variety of materials. For example, bulb 160 can be kidney shaped as shown in FIGS.

1-9. A kidney shaped bulb is advantageous over a round bulb for activation/contact on the alar tissue and the outside of the nose/lip. This prevents the spring from contacting the skin and it increases the surface area contact between the bulb and the tissue/skin.

Figure 11:
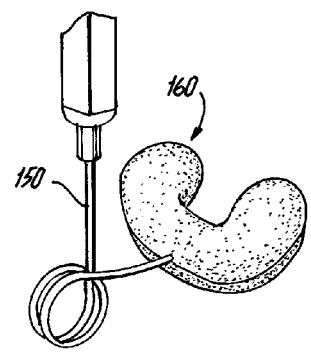
FIG. 11 is an enlarged, partial perspective view of the bottom of the device shown in FIG. 10.
Figure 12:
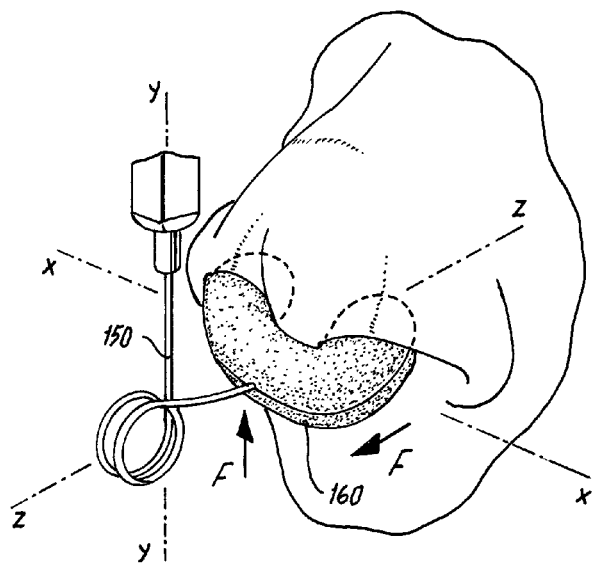
FIG. 12 is an enlarged, partial perspective view of the bottom of the rod, the rod connector, the spring, the bulb and nose/face of the infant shown in FIG. 10. The bulb is shown inside and outside the nasal passage. The desired component forces (F) on the nasal tissue are shown on the Y and Z axes.

For a bilateral case where forces are desired in each nostril of the infant, as shown in FIGS. 10-12, the device can be used with one spring 150 connected to a bilateral bulb or the device can include two springs 150 with two separate unilateral bulbs 160 as shown in FIG. 7.

The bulb may be made of an acrylic material or another material that does not cause irritation when placed inside the nose, such as, for example plastic or silicone, or a combination thereof.

In the embodiment shown in the figures, the bulb 160 is shown non-removable from the end of spring 150. The end of the spring may compression fit inside an opening in the bulb 160. Alternatively, and more preferred, the end of spring 150 is configured without a straight pointed shape such that the bulb, prior to drying or curing, such as with a heated acrylic bulb when formed on the end of the spring 150, becomes fixed to the end of the spring 150. For example, the end of the spring 150 could be configured with a hook, bend, elbow, coil, etc.

Alternatively, the bulb 160 could be removable with, for example, a threaded opening for attachment onto threads on the end of the spring 150.

For purposes of explaining how the device is used, the device is fitted onto the head of the infant with the front connector 118 positioned at the middle of the infant's forehead. The size of the fastener 110 is adjusted to fit snugly on the infant. A rod 130, spring 150 and bulb 160 are assembled for the desired length and for the patient's particular case. The first end of the rod 130 (opposite the bulb 160) is inserted into the aperture 122 in the rod support 120 until the bulb 160 is in the desired position inside the nasal passage of the infant. The location of the bulb (height, angle, position medially, etc.) and/or the spring configuration/shape is adjusted to achieve the desired pressure on the tissue/skin of the infant.

During treatment of the infant over the course of 4-6 months, when using the device according to the invention, the position of the bulb requires adjustment in at least one direction, most commonly superiorly along the Y-Y axis but also medially and anteriorly in the X-X and Z-Z axes. Such adjustments can be accomplished by modifying the shape of the metal spring 150, by removing and replacing the metal spring 150 with a different shaped spring, by adjusting the height of the rod 130 on the rod support 120, by removing and replacing the rod 130 with a rod having a different length, by repositioning the fastener 110 and/or front connector 118 a little higher on the forehead of the infant, by removing and replacing the bulb 160 with a bulb of different shape and configuration, and/or by adjusting the height of the connector 140 at the bottom of the rod 130. Any one or more of these adjustment methods and structures are included in the scope of the invention. At least 5-7 mm of height adjustment in the Y-Y axis is desired and possible using the present invention.

I claim:

1. An extraoral device for treating cleft lip and palate comprising:
    an adjustable head fastener comprising straps and a front connector, said front connector having a comfort pad on an inside of said front connector and a rod support fixedly connected to an outside of said front connector;
    said rod support comprising an aperture configured to receive a rod to slidably connect to said rod, said front connector further comprising a threaded aperture with a set screw capable of securing the rod to said rod support;
    a rod having a first end and a second end, said first end slidably connected to said rod support and lockable in a set position using said set screw;
    a spring having a first end and a second end, said first end of said spring attached to said second end of said rod; and
    a kidney shaped bulb having a convex side and a concave side, said bulb attached to said second end of said spring at about a middle of the convex side of said bulb.

2. The device according to claim 1, wherein the first end of said spring is removably attachable to said second end of said rod.

3. The device according to claim 1, wherein said spring is configured in a shape of a double helical coil.

4. The device according to claim 1, wherein said spring is configured in a shape of a triple helical coil.

5. The device according to claim 1, wherein the bulb is removeably attached to said second end of said spring.

6. The device according to claim 1, wherein said bulb material is made of at least one material from the group consisting of acrylic, silicone, and plastic.

7. The device according to claim 1, wherein said rod support is hingedly connected to the front connector.

8. An extraoral device for treating cleft lip and palate comprising:
    an adjustable head fastener comprising straps, a front connector having an inside and an outside, and a rod support fixedly connected to an outside of the front connector, said rod support having an aperture configured to slidably connect to a rod, said front connector further comprising a threaded aperture with a set screw capable of securing the rod to said rod support;
    said rod having a first end and a second end, said first end of said rod slidably connected to said rod support and lockable in a set position using said set screw;
    a stainless steel wire spring having a first end and a second end, said first end of said spring fixedly attached to said second end of said rod; and
    a bulb fixedly attached to said second end of said spring.

9. The device according to claim 8, wherein said spring is configured in a shape of a double helical coil.

10. The device according to claim 8, wherein said spring is configured in a shape of a triple helical coil.

11. The device according to claim 8, wherein the bulb is kidney shaped for use in one nostril of an infant with unilateral cleft lip and palate.

12. The device according to claim 11, said bulb having a convex side and a concave side, wherein said second end of said spring attaches to said bulb at about a middle of said convex side of said bulb.

13. The device according to claim 8, wherein the bulb is about U-shaped for use in two nostrils for treating bilateral cleft lip and palate.

14. The device according to claim 8, wherein said bulb is made of at least one material from the group consisting of acrylic, silicone, and plastic.

15. The device according to claim 8, wherein said rod is comprised of a hollow metal tube.

* * * * *